United States Patent
Callister et al.

(10) Patent No.: US 7,694,683 B2
(45) Date of Patent: Apr. 13, 2010

(54) METHODS AND DEVICES FOR OCCLUDING BODY LUMENS AND/OR FOR DELIVERING THERAPEUTIC AGENTS

(75) Inventors: Jeffrey P. Callister, Redwood City, CA (US); William S. Tremulis, Redwood City, CA (US)

(73) Assignee: Conceptus, Inc., Mountain View, CA (US)

( * ) Notice: Subject to any disclaimer, the term of this patent is extended or adjusted under 35 U.S.C. 154(b) by 0 days.

(21) Appl. No.: 10/880,355

(22) Filed: Jun. 28, 2004

(65) Prior Publication Data

US 2005/0045183 A1   Mar. 3, 2005

Related U.S. Application Data

(63) Continuation-in-part of application No. 08/770,123, filed on Dec. 18, 1996, now Pat. No. 7,073,504.

(60) Provisional application No. 60/483,587, filed on Jun. 27, 2003.

(51) Int. Cl.
*A61F 6/06* (2006.01)
*A61B 17/08* (2006.01)

(52) U.S. Cl. .................. 128/831; 128/832; 606/157

(58) Field of Classification Search ............ 606/157, 606/158, 213, 191, 193, 194, 198, 200; 424/422, 424/423, 430, 433; 623/1.46, 1.39, 1.4, 1.42; 128/832, 830, 831, 833, 842, 843; 604/502
See application file for complete search history.

(56) References Cited

U.S. PATENT DOCUMENTS

| | | | | |
|---|---|---|---|---|
| 3,334,629 A | * | 8/1967 | Cohn | 606/194 |
| 3,687,129 A | * | 8/1972 | Nuwayser | 606/191 |
| 3,865,108 A | * | 2/1975 | Hartop | 424/430 |
| 3,991,760 A | * | 11/1976 | Drobish et al. | 128/832 |
| 4,279,252 A | | 7/1981 | Martin | |
| 4,579,110 A | * | 4/1986 | Hamou | 128/831 |
| 5,024,671 A | * | 6/1991 | Tu et al. | 623/1.42 |
| 5,152,777 A | * | 10/1992 | Goldberg et al. | 606/200 |
| 5,256,146 A | * | 10/1993 | Ensminger et al. | 606/198 |
| 5,433,218 A | * | 7/1995 | Wildemeersch | 128/833 |
| 5,601,600 A | * | 2/1997 | Ton | 606/198 |
| 5,634,942 A | * | 6/1997 | Chevillon et al. | 606/200 |
| 5,704,910 A | * | 1/1998 | Humes | 604/502 |
| 5,792,154 A | * | 8/1998 | Doan et al. | 606/151 |
| 5,935,137 A | | 8/1999 | Saadat et al. | |
| 5,979,446 A | * | 11/1999 | Loy | 128/830 |
| 5,980,554 A | * | 11/1999 | Lenker et al. | 606/198 |
| 6,099,562 A | * | 8/2000 | Ding et al. | 623/1.46 |
| 6,432,116 B1 | | 8/2002 | Callister et al. | |
| 6,517,559 B1 | | 2/2003 | O'Connell | |
| 6,526,979 B1 | * | 3/2003 | Nikolchev et al. | 128/831 |

* cited by examiner

*Primary Examiner*—Julian W Woo
(74) *Attorney, Agent, or Firm*—Blakely, Sokoloff, Taylor & Zafman llp

(57) ABSTRACT

Devices, systems and methods for occluding the lumens of anatomical passageways and/or for delivering drugs or other substances to the bodies of human or animal subjects.

26 Claims, 13 Drawing Sheets

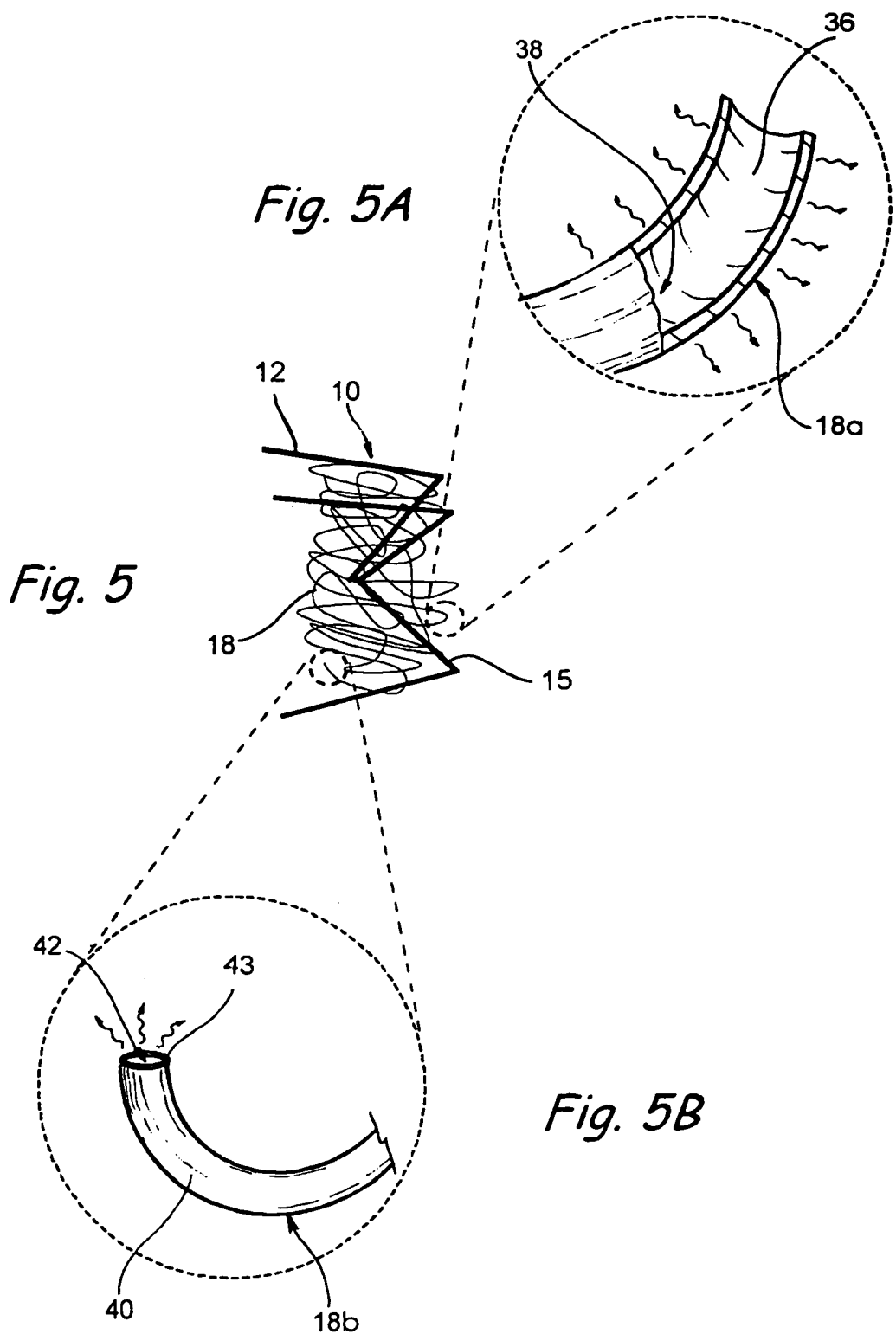

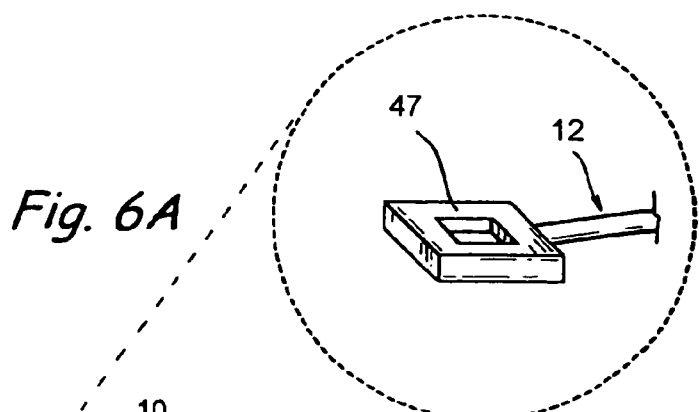
Fig. 6A
Fig. 6
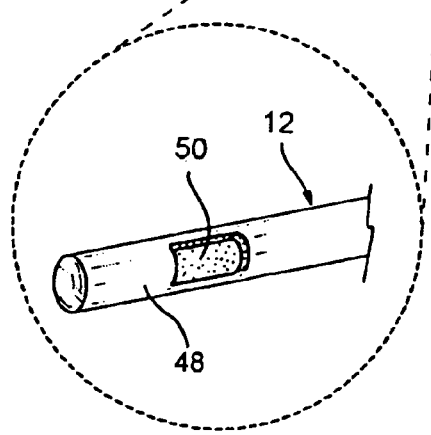
Fig. 6B
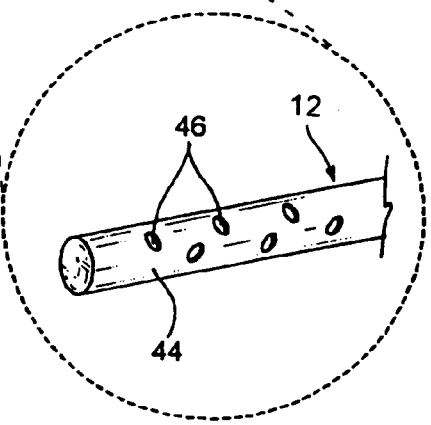
Fig. 6C

METHODS AND DEVICES FOR OCCLUDING BODY LUMENS AND/OR FOR DELIVERING THERAPEUTIC AGENTS

RELATED APPLICATIONS

This patent application claims priority to U.S. Provisional Patent Application No. 60/483,587 filed on Jun. 27, 2003, the entirety of which is expressly incorporated herein by reference. Additionally, this application is a continuation-in-part of co-pending U.S. patent application Ser. No. 08/770,123 (Callister et al.) filed on Dec. 18, 1996 and published on Jan. 31, 2002 as U.S. patent application 2002/0013589A1, the entirety of which is expressly incorporated herein by reference.

FIELD OF THE INVENTION

This invention relates generally to medical devices, methods and systems and more particularly to medical devices and more particularly to devices that are implanted within body lumens (e.g., fallopian tubes, vas deferens, bronchi, blood vessels, etc.) to occlude that body lumen and/or to deliver therapeutic substance(s) for local or systemic therapeutic effect.

BACKGROUND OF THE INVENTION

There exist various situations in which it is desirable to implant embolic or occlusive devices within lumens or anatomical passageways within the bodies of human or animal subjects. In at least some of those situations, it is additionally desirable to deliver a substance (e.g., a drug, a protein, cells, a biological material, a chemical substance, a gene therapy preparations, etc.) for at least an initial period of time following implantation of the embolic or occlusive device.

For example, it has been known to implant occlusive devices into the fallopian tubes of females or the vas deferens of males for contraceptive purposes. Examples of implantable occlusive devices useable for such purposes are described in U.S. Pat. No. 6,096,052 (Callister et al.) entitled Occluding Device and Method of Use and U.S. Pat. No. 6,432,116 (Callister et al.) entitled Occluding Device and Method of Use, the entireties of both such United States Patents being expressly incorporated herein by reference. Some of these devices have been constructed and/or implanted in a manner to facilitate tissue ingrowth subsequent to implantation of the device such that, after such tissue ingrowth has occurred, the ingrown tissue alone or in combination with the implanted device will provide complete occlusion of the lumen of the fallopian tube or vas deferens. Thus, during the period between implantation of the device and completion of the lumen-occluding tissue ingrowth, the lumen of the fallopian tube or vas deferens may remain at least partially open. Thus, it may be desirable to provide alternative contraceptive means to prevent unwanted pregnancy during the period between implantation of the device and completion of the lumen-occluding tissue ingrowth.

The above incorporated U.S. patent application Ser. No. 08/770,123 (Callister et al.) described various embodiments of lumen occluding devices that may be used to occlude the lumen of a fallopian tube or vas deferens, some of which may deliver a drug, such as a contraceptive agent.

There remains a need in the art for the development of new implantable lumen occluding devices that are capable of delivering a substance (e.g., a drug, a protein, cells, a biological material, a chemical substance, a gene therapy preparations, etc.).

SUMMARY OF THE INVENTION

The present invention provides devices that may be implanted into a body lumens (e.g., fallopian tube, vas deferens, bronchus, blood vessel or other anatomical passageway or lumen) of a human or veterinary subject to occlude that body lumen and/or to deliver a substance (e.g., a drug, a protein, cells, a biological material, a chemical substance, a gene therapy preparations, etc.) for at least a period of time following implantation of the device.

In accordance with the invention there is provided an implantable occlusion and/or substance delivery device of the foregoing character that comprises; a) an expandable intraluminal member which is i) disposable in a first configuration wherein it is sufficiently compact to be advanced into the body lumen and ii) subsequently expandable to a second configuration wherein the intraluminal member becomes implanted within the body lumen; and., b) a quantity of a substance disposed on or in the device such that the substance will be delivered from the intraluminal member into some target tissue for at least some period of time following implantation of the intraluminal member within the body lumen. In some embodiments, the intraluminal member may include a mesh material or other matrix designed to facilitate cellular or tissue ingrowth such that cells or tissue that ingrow into the device will effect occlusion of the body lumen in which the device is implanted. The present invention additionally includes systems wherein the implantable occlusion and/or substance delivery device is used in combination with a delivery catheter and/or guidewire and/or endoscopic device.

Further in accordance with the invention, there are provided methods for sterilization or contraception wherein a lumen occluding and/or substance delivering device of the foregoing character is implanted in a fallopian tube of a female subject or the vas deferens of a male subject. In such applications, the substance disposed on or in the device may comprise a contraceptive or spermicidal agent that will be delivered by the device in a concentration and form that is effective to cause a contraceptive effect in the subject, at least during a period of required for the implanted device to effect complete occlusion of the fallopian tube or vas deferens. Still further in accordance with the invention, there are provided methods for treating disorders or injuries of the lung by implantation of a lumen occluding and/or substance delivering device of the foregoing character within a bronchus, bronchiole or other anatomical passageway within the lung. In such applications, the device may occlude a bronchus to stop the flow of inspired air to a portion of the lung (e.g., a lobe or portion of a lobe) that is diseased or injured. In such applications, the substance disposed on or in the device may comprise an agent that causes a therapeutic effect in the lung such as an antimicrobial agent, mucolytic agent, bronchodilator, antiinflamatory, expectorant, antineoplastic agent, chemotherapeutic agent, immunomodulator, etc.

Still further in accordance with the invention, there are provided varied and universal methods for treating disorders or injuries of human or animal subjects by implanting a device of the foregoing character in a body lumen (e.g., a man-made lumen or a natural passageway within the body such as a blood vessel, lymphatic duct, duct of the biliary tree, etc.) so as to cause occlusion of that body lumen and to release a therapeutically or diagnostically effective amount of a substance for at least some period of time following implantation of the device.

Further aspects, elements and embodiments of the invention will become apparent to those of skill in the art upon reading and consideration of the detailed description set forth herebelow and the accompanying drawings to which it refers.

BRIEF DESCRIPTION OF THE DRAWINGS

FIG. 5 is an enlarged perspective view of a lumen occluding/substance delivery device of the present invention having an optional substance delivery and/or ingrowth supporting matrix thereon.

FIG. 5A is an enlarged, cut away view of a portion of the substance delivery and/or ingrowth supporting matrix of the device of FIG. 5 illustrating one way in which the substance delivery and/or ingrowth supporting matrix may be constructed to deliver a substance following its implantation within the body of a patient.

FIG. 5B is an enlarged, cut away view of a portion of the substance delivery and/or ingrowth supporting matrix of the device of FIG. 5 illustrating another way in which the substance delivery and/or ingrowth supporting matrix may be constructed to deliver a substance following its implantation within the body of a patient.

FIG. 6 is an enlarged perspective view of a lumen occluding/substance delivery device of the present invention having an optional substance delivery and/or ingrowth supporting matrix thereon and wherein portions of the device are constructed to carry out controlled delivery of a substance following its implantation within the body of a patient.

FIG. 6A is an enlarged view of a portion of the device of FIG. 6 illustrating one way in which the device may be constructed to deliver a substance following its implantation within the body of a patient.

FIG. 6B is an enlarged view of a portion of the device of FIG. 6 illustrating another way in which the device may be constructed to deliver a substance following its implantation within the body of a patient.

FIG. 6C is an enlarged view of a portion of the device of FIG. 6 illustrating yet another way in which the device may be constructed to deliver a substance following its implantation within the body of a patient.

DETAILED DESCRIPTION

Figure 1A:
FIG. 1A is a side view of one embodiment of a lumen occluding and/or substance delivery device according to the present invention, disposed in a collapsed configuration.
Figure 1B:
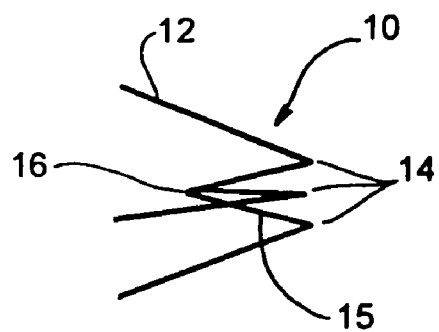
FIG. 1B is a side view of the device of FIG. 1A, disposed in an expanded configuration.
Figure 1C:
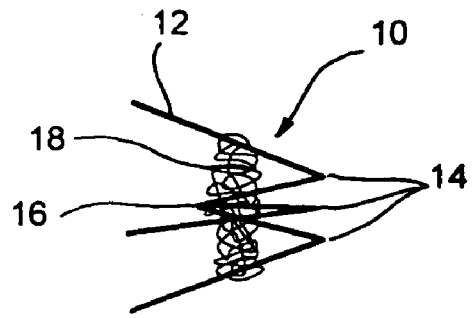
FIG. 1C is a side view of the device of FIGS. 1A and 1B, disposed in an expanded configuration and having an optional substance delivery and/or ingrowth supporting matrix thereon.

In particular, the present invention relates to devices, methods and systems for the occlusion of various passageways of the body including the delivery of therapeutic substances by placement of drugs or drug secreting material on or within such devices. In the various aspects of occluding body passageways, one object of this invention that is particularly useful is for the occlusion of the fallopian tubes to effect permanent contraception. Although the occlusion of the fallopian tubes will be discussed in detail, it can be appreciated that the devices, methods and systems described herein can easily be adapted to occlude the vas in the male patient, arteries or veins in the nidus of an arterial-venous malformation, patent ductus arteriosis in infants, as well as feeding arteries to cancerous tumors, among other passageways. The invention also provides means for delivering vessel supporting devices such as coronary stents or venous or arterial embolic filters, to the desired location through a steerable system. Although any of these procedures may benefit from the inventions described herein, one particularly useful and immediate benefit for these devices, methods and systems is in the delivery of occlusion devices to the fallopian tubes for contraceptive purposes. At least some of these objectives will be met by the novel inventions, devices, methods and systems described hereinbelow. This invention in some embodiment also provides for delivery of therapeutic substances to desired locations and in advantageous manners Those skilled in the art will recognize that various combinations, modifications, and equivalents of the inventions described herein can be used without departing from the scope of these inventions.

The present invention provides devices, methods and systems for the occlusion of various body passageways. It also includes catheter systems for the delivery of embolic devices as well as vascular stents, especially small diameter stents as may be desirable in the coronary or cerebral vasculature. Typically these devices are delivered either by direct placement or by using "over-the-wire" (OTW) designs or techniques. Although OTW designs allow for steerability of the guide wires and delivery catheters, the devices typically must have in inner diameter larger than the removable guide wire with which it is used. The diameter of the guide wire, however, may be too large, even it its smallest functional diameter, to allow for a small enough collapsed profile to transverse through the target passageway. The alternative means of using a pushing device proximal to the collapsed device allows for the device to have a very small collapsed profile since no guide wire needs to pass through it, however such systems may have reduced steerability of the system through the body lumens, particularly distal to the collapsed device. For these reasons and others it would be desirable to have a small diameter system that still allows for steerability of the guide wire while advancing through the body passageways.

Figure 2A:
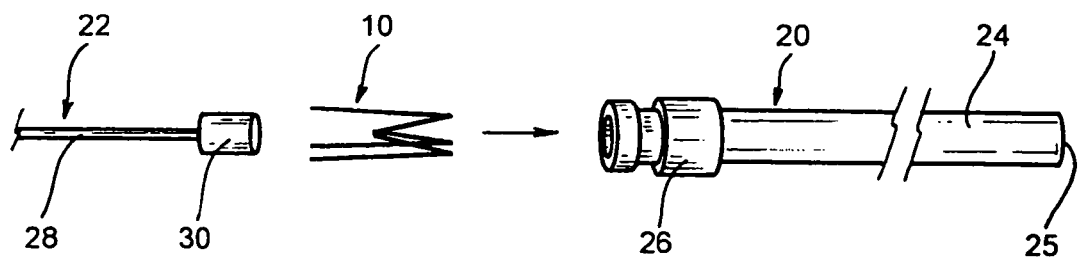
FIG. 2A is an exploded perspective view of one embodiment of system of the present invention comprising a lumen occluding/substance delivery device as shown in FIGS. 1A and 1B, in combination with a delivery cannula and a pusher device.
Figure 2B:
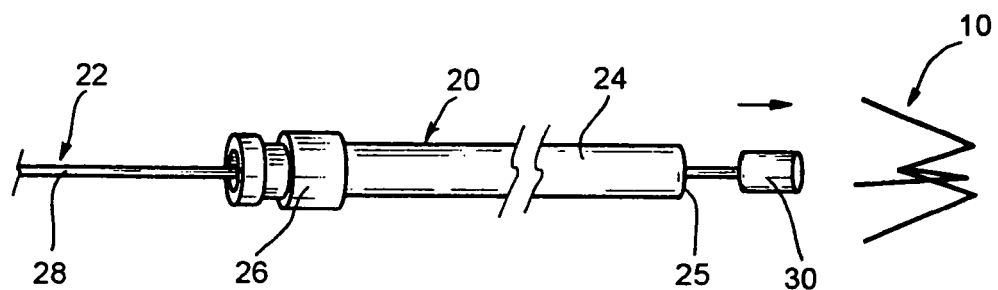
FIG. 2B is a perspective view of the system of FIG. 2A wherein the pusher has been used to expel the lumen occluding/substance delivery device out of the distal end of the delivery catheter.

Referring now to the examples of the invention shown in the drawings, in accordance with one aspect of this invention, there is provided an expandable lumen occluding and/or substance delivery device 10 that is delivered through a suitable delivery cannula 20 (e.g., a rigid or flexible tube or catheter such as a microcatheter or hypotube). As shown in FIGS. 2A and 2B, the device 10 may be placed in its collapsed configuration and inserted into the lumen of a delivery cannula 20. The delivery cannula 20 comprises a wall 24 that devices a lumen that extends through the cannula 20. A hub 26 may be formed on the proximal end of the delivery cannula 20. After the device 10 has been advanced into the lumen of the cannula, the cannula wall 24 will constrain the device 10 in a relatively collapsed configuration while the device 10 remains inside lumen. In this example, a pusher device 22 comprising an elongate rod 28 and pusher head 30, is useable to facilitate expulsion or release of the device 10 from the delivery cannula 20. Upon exiting the delivery cannula 20, the device 10 resumes its expanded or remembered configuration by the release of a radially expansive force. Alternatively, the device 10 may expand or assume a larger diameter as a result of shape memory (e.g., becoming larger in diameter as a result of temperature change) or other shape altering properties or instrumentalities.

Although the pusher 28 with bulbous pusher head 30 may, in some embodiments, comprise a "pusher wire", it will be understood that the device 10 may be end-loaded into the cannula 20 in the compressed configuration with the pusher 28 in place immediately proximal to the device. When the delivery catheter 20 is placed in the desired location in the body, for example in the fallopian tube, then the cannula 20 may then be withdrawn in the proximal direction while the pusher 28 is held stationary in the longitudinal direction. This has the effect of laying down the expanding occlusive device without actually pushing it forward in the potentially fragile body lumen such as a fallopian tube or tubule in the lung. In this way any injury to the body structure that would otherwise occur by pushing the expanded device forward through the body lumen is avoided. Also, by back-loading the device into the distal end of the delivery catheter, it need not be pushed through the entire length of the catheter. Thus the distal end portion of the delivery cannula 20 may be reinforced, perhaps with slippery substance that makes movement of the device smooth and convenient, and may be reinforced, perhaps with stainless steel wire or the like which would be undesirable for flexibility if the entire length of the catheter had to be so reinforced. In those cases, the "pusher" does not expel the device forward and push it longitudinally thorough the body lumen, but rather stabilizes it as the catheter is withdrawn from over it. Nonetheless, with that understanding, the term "pusher wire" will be used in this patent to describe that device.

In the particular embodiment of the device 10 shown in the drawings, a plurality of first leg segments 15 emanate from a central apex 16. Each first leg segment 15 is joined at an angle with a second leg segment 12, thereby forming a plurality of secondary apices 14, as shown. When the device 10 is expanded or allowed to expand within a body lumen, the second leg segments 12 will contact and exert a constant outward force on the wall of the body lumen in which the device 10 is positioned thereby maintaining in a substantially stationary position within that body lumen. Sometimes at least one of the second leg segments 12 may be formed of thin, relatively rigid material and/or may comprise a projection (e.g., a hook, barb, etc.) that will lodge in the lumen wall to secure the device 10 in place.

It will be appreciated that, although the device 10 may comprise a single unit as shown in the figures, the invention includes systems or embodiments wherein a plurality of these single unit devices 10 are aligned or positioned adjacent to each other to form a multi-unit occluding system or structure within a body lumen. In such embodiments, the aligned or adjacently positioned single unit devices 10 may optionally be joined or connected to one another to form a unitary structure. In this regard, it will be appreciated that two or more of the devices 10 (separate or conjoined) may be loaded into the lumen of the delivery cannula 20 an expelled from the distal end 25 of the delivery cannula 20 by the pusher 22. Alternatively, a plurality of the devices 10 may be loaded into and expelled from the delivery cannula 20, one at a time, thereby implanting a plurality of the devices 10 in series within a body lumen.

In some embodiments, the configuration of the device may be modified from that shown in the figures to a generally tubular shape that is expandable and collapsible, as with a stent. Devices of this general nature are described in U.S. Pat. No. 6,096,052 (Callister et al.) and U.S. Pat. No. 6,432,116 (Callister et al.), the complete disclosures of which are incorporated herein as if set forth in full.

The device 10 may be configured, constructed or contain materials that support or facilitate tissue ingrowth. As used herein, the term tissue ingrowth includes but is not limited to cell mulitiplication and/or or growth resulting in tissue formation into, onto, or surrounding a particular region and/or into, onto or surrounding an obstructive device. This may be epithelization, scar formation, or other cell growth or multiplication. For example, the leg portions 12, 15 and/or matrix 18 may incorporate materials that promote epithelialization, endothelialization, granulation or other proliferative or tissue growth response within the body to create a more effective occlusion of the passageway or to result in a more secure attachment of the occlusion device to the walls of the body lumen. For instance, polyester fibers may be attached to the device 10 such that tissue ingrowth into and around the device will form a plug and thereby occlude the lumen in which the device is implanted. In some embodiments, a volitionally deployable wall abrading projection (e.g., a flare or projection) may be provided on the distal portion of the cannula 20 and/or on the device 10 to abrade or denude the epithelial layer of the fallopian tube FT or other body lumen in which the device 10 is implanted, thereby enhancing the tissue ingrowth response. Such volitionally deployable wall abrading projection could both be deployed when entering the body lumen and/or when deploying the device 10.

Additionally, as described in detail herebelow, substances such as therapeutic agents, drugs, (e.g., contraceptive hormones, spermicidal agents, spermatogenesis inhibitors, antimicrobials, antibiotics, antifungals, chemotherapeutic agents, biologics, etc.) or biological factors (VEGf, FGF, etc.) may be incorporated on or within the device in order to bring about some desired effect (e.g., to accelerate tissue ingrowth, prevent/treat infection, cause drug-induced contraception for at least a sufficient period of time to allow the implanted lumen occluding device to become fully functional, treat a disease or disorder in the adjacent tissue, etc). When the implantable device of this invention is used to block the lumen of a fallopian tube, vas deferens or other body lumen for the purpose of deterring pregnancy, the lumen blocking efficacy of the device (and thus its reliability as a contraceptive measure) may not become maximized for several weeks or months after the initial implantation of the device 10 as such amount of time may be required for the implanted device 10 to become fully epithelialized or for other tissue ingrowth to become complete. In such instances, a quantity of a contraceptive agent and/or spermicidal agent may be incorporated on or in the device so as to provide for drug-induced contraception for a period of time that is at least sufficient to allow the lumen blocking efficacy of the device to become maximized. Examples of specific substances (e.g., drugs, therapeutic agents, biological factors, etc.) that may be incorporated into or onto the device 10 of this invention or any other lumen occluding device are described herebelow.

Figure 3A:
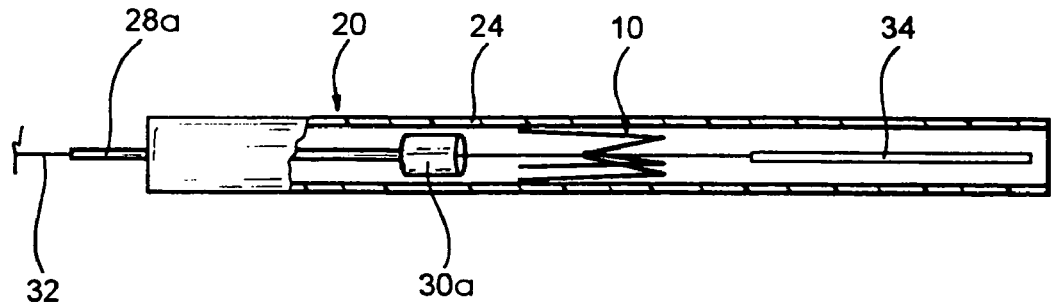
FIG. 3A is a partial longitudinal sectional view of another embodiment of system of the present invention designed for over-the-wire delivery of the implantable device.
Figure 3B:
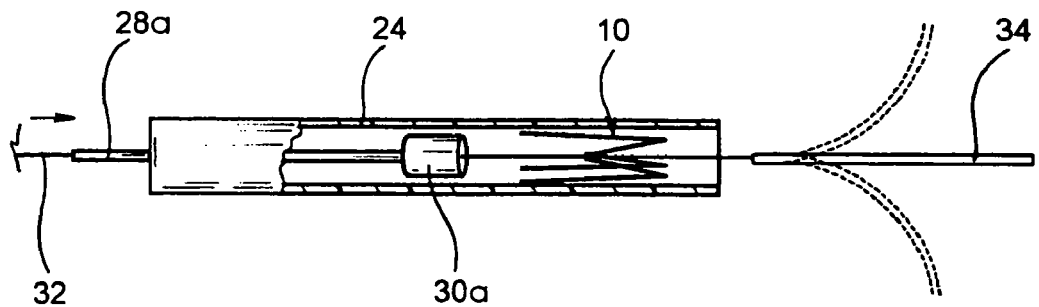
FIG. 3B is a showing of the system of FIG. 3A with the guidewire protruding from the distal end of the delivery catheter.

FIGS. 3A-3B show a system for OTW delivery of the lumen occluding and/or substance delivery device 10. This system generally comprises the lumen occluding and/or substance delivery device 10, a delivery cannula 20 as described above and a modified pusher device 28a that has a guidewire lumen extending longitudinally therethrough such that a guidewire 32 may pass through the lumen of the pusher device 28a, through the lumen occluding and/or substance delivery device 10 and through the lumen of the delivery cannula 20, as shown in FIG. 3A. Alternatively, and not shown in the figures, the pusher head 30a may have a groove therein through which the guidewire 32 may slide so that it will be located longitudinally side-by side with the pusher 29a. Optionally, the guidewire 32 may have a distal portion 34 that is more flexible than the proximal portion of the guidewire and/or is otherwise deflectable, flexible or steerable. In operation, the guidewire 32 may be advanced into a desired body lumen (e.g., a fallopian tube) into which it is desired to implant the lumen occluding and/or substance delivery device 10. Thereafter, the delivery cannula 20 having the device 10 and pusher 28a within its lumen may be advanced over the previously inserted guidwire to a location where the distal end of the delivery cannula 20 is adjacent to the location where it is desired to implant the device 10. Thereafter, the pusher 28a may be advanced over the guidewire 32 such that the enlarged distal end 30a of the pusher 28a will expel the lumen occluding and/or substance delivery device 10 out of the distal end of the delivery cannula 20. The device 10 will then self expand within the body lumen such that the second leg segments 12 of the device engage the wall of the body lumen. Thereafter, the delivery cannula 20, pusher 28a and guidewire 32 may be removed, leaving the device 10 implanted within the body lumen.

Figure 4:
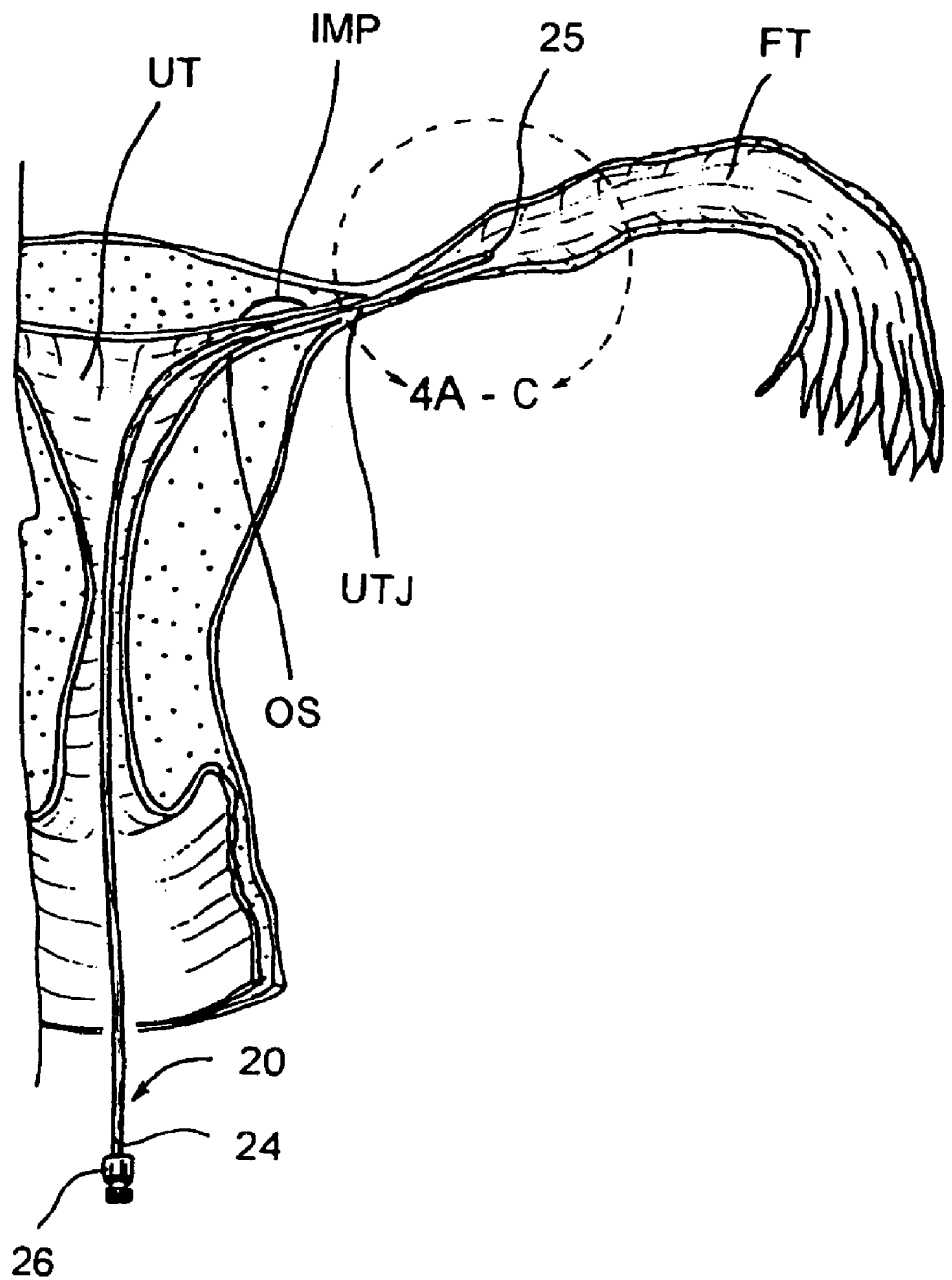
FIG. 4 is a sectional showing of the uterus and left fallopian tube of a human patient having the over-the-wire system of FIGS. 3A and 3B inserted into the left fallopian tube.
Figure 4A:
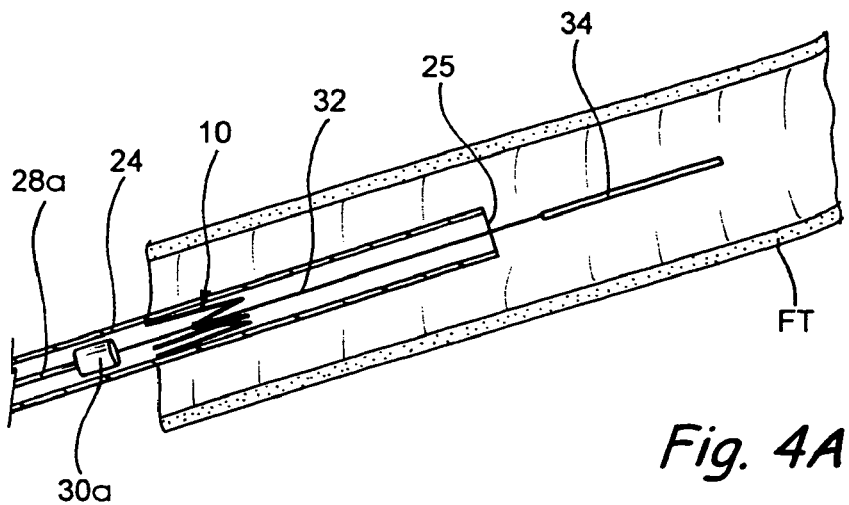
FIGS. 4A-4C show three steps in a procedure wherein the system shown in FIG. 4 is used to implant a lumen occluding/substance delivery device in the patient's left fallopian tube.
Figure 4B:
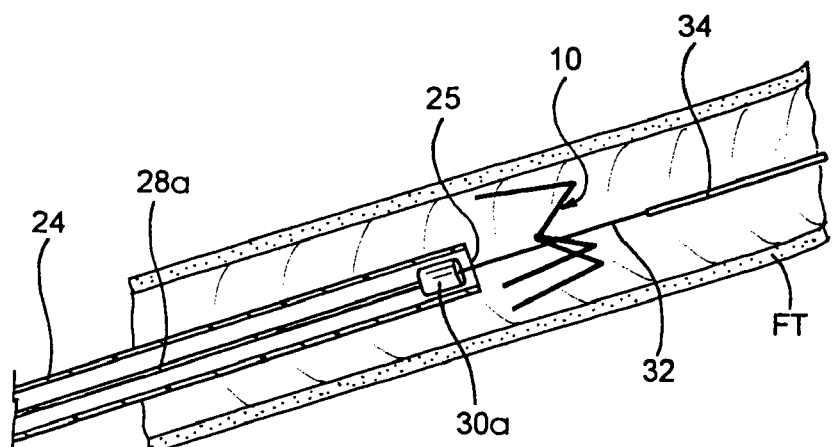
Figure 4C:
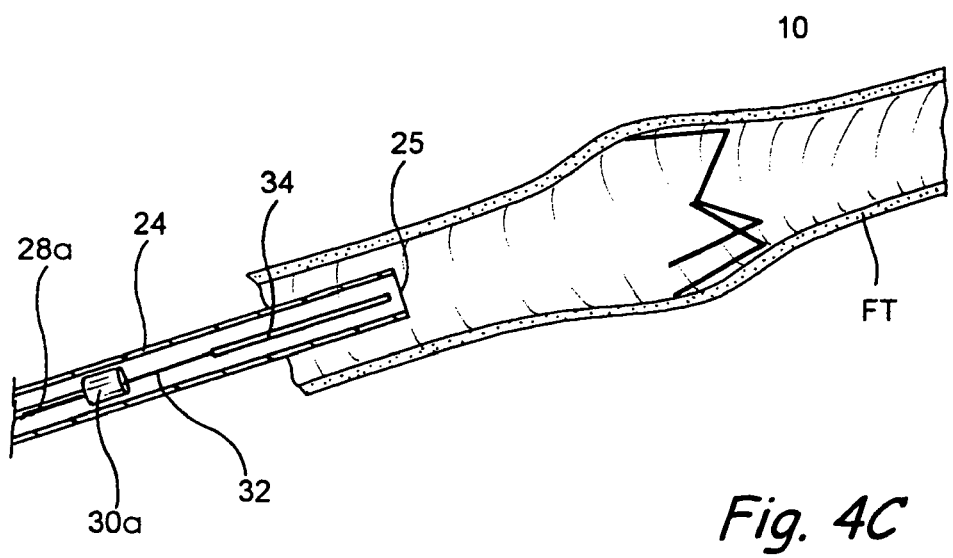

FIGS. 4-4C show a specific procedure in which the OTW system shown in FIGS. 3A-3C is used to implant a lumen occluding and/or substance delivery device 10 within a fallopian tube. Initially, the guidewire 32 is advanced through the uterus UT and into the fallopian tube FT. The delivery catheter 20 (with the collapsed device 10 and pusher 28a positioned therein) is advanced over the guidewire 32, as seen in FIG. 4A. Thereafter, as shown in FIG. 4B, the pusher 28a is advanced over the guidewire 32 such that the enlarged distal end 30a of the pusher 28a pushes the device 10 out of the distal end 25 of the delivery cannula 20. Upon exiting the distal end 25 of the delivery cannula 20, the device 10 self expands to its expanded configuration whereby the second leg segments 12 of the device 10 are urged against the wall of the fallopian tube FT, thereby holding the device 10 in a fixed position, as shown in FIG. 4C. The delivery cannula 20, pusher 28a and guidewire 32 are then withdrawn through the uterus UT and removed, leaving the device 10 implanted within the fallopian tube FT. Following implantation, tissue will ingrow into the device 10 to cause complete occlusion of the fallopian tube FT. At least during the period of time during which such tissue ingrowth is occurring, the device 10 may elute a substance (e.g., a contraceptive or spermicidal substance) in an amount that causes a desired therapeutic effect (e.g., contraception or spermicide) in the patient. Optionally, the device 10 may include a matrix 18, as described above, to facilitate the desired tissue ingrowth and/or to deliver the desired substance.

If more than one device 10 is to be implanted within the subject's body, there is no need to remove the delivery cannula 20 to deliver the additional devices. For instance, if devices 10 are to be implanted in both fallopian tubes FT, the delivery catheter 20 may initially contain two devices 10, one for each fallopian tube FT. In such an instance, the physician may insert the delivery catheter 20 through the uterus of the patient, and deliver one device to the first of two fallopian tubes FT, and, after delivery of the first device 10, the physician may then insert the delivery catheter 20 into the other fallopian tube 20 and deploy the second device 10 into the other fallopian tube FT without having to withdraw the delivery cannula 20 from the uterus UT. This has the advantage of speeding the overall procedure time since there is no need to remove and replace a delivery cannula 20 for each fallopian tube FT. Additionally, overall costs for the procedure are reduced since only one delivery cannula 20 and one pusher 28a are used to place two devices 10. Alternatively, the present invention also allows for the lumen occluding and/or substance delivery device 10 to be advanced through the entire length of the delivery cannula 20. In such an instance, the delivery cannula 20 is advanced to the location where the device 10 is to be placed. The guide wire 32 may aid in positioning the delivery cannula 20. Following acceptable placement of the delivery cannula 20, the guide wire 32 may be removed from the delivery cannula 20 and the first occlusion device 10 may then be placed in a collapsed configuration and loaded into the lumen of the cannlua 20 through its proximal end. After the device 10 has been located within lumen of the delivery cannula 20, a standard pusher 38 (see FIGS. 2A and 2B) may be used to advance the device 10 through the length of the delivery cannula 20 and out of its distal end 25. The device 10 will then expand and become implanted within the lumen of the fallopian tube FT in the manner described hereabove.

In accordance with yet another aspect of this invention, it will be appreciated that the enlarged pusher head 30 or 30a could actually be mounted on the guidewire 32 at a location proximal to the device 10 such that, as the guidewire 32 is advanced in the distal direction (or as the cannula 20 is withdrawn in the proximal direction) the pusher head 30 or 30a will push the device 10 along with it.

One major advantage to the type of system shown in FIGS. 4A-4B is that the entire system may be steerable, since the distal portion 34 of the guide wire 32 may be constructed to be torqued or steered through the body passageways to its desired location. A small hole may be formed in the central apex 16 of the device 10 and the guidewire 32 may pass through that hole. Thus, such torquing the guide wire 32 may have no significant effect on the device 10 since even in its collapsed state within the delivery cannula 20 there is still a small hole through the device 10 through which the guide wire 32 passes.

The distal portion 34 of the guide wire 32 may be flexible and may incorporate a conventional spring tip or, alternatively, it may be made of or incorporate a plastic or Teflon coating to prevent any snagging of any attached fibers on the occlusion device. Additionally, the device 10 may be positioned on a reduced diameter segment of the guidewire 32 and such reduced diameter segment may be longer than the device 10. This will permit a limited amount of axial movement of the guide wire 32, either proximally or distally, to further aid in the bendability and/or steerability of the system. Delivery cannula 20 may thus be able to provide either more or less support for the guide wire support, depending on the circumstances and the tortuosity of the vasculature or passageway being navigated. In such embodiments wherein the guide wire 32 is axially moveable over a limited range but not completely removeable may allow the use of a steerable guide wire 32 having a relatively large diameter distal portion in combination with a low profile delivery cannula 20 (e.g., a delivery cannula 20 that has a diameter that is the same as or even smaller than the diameter of the distal portion of the guide wire 32). It will be appreciated by those of skill in the art that the device 10 may be self-expanding, or it may be pressure expanded (e.g., plastically deformable) through the use of a balloon catheter or the like. In some self-expanding embodiments, the device 10 may assume its expanded configuration as a result of temperature shape memory or release of compression, or any other appropriate means. As the device 10 assumes its expanded configuration as shown in FIG. 4C, it may expand across the body lumen in which it is positioned and assume a configuration wherein any guidewire passage hole or opening formed in the device 10 will be large enough to allow the guidewire 32 to be retracted through the expanded device 10 and back into the lumen of the delivery cannula 20 for withdrawal, leaving the device 10 in place.

Figure 9:
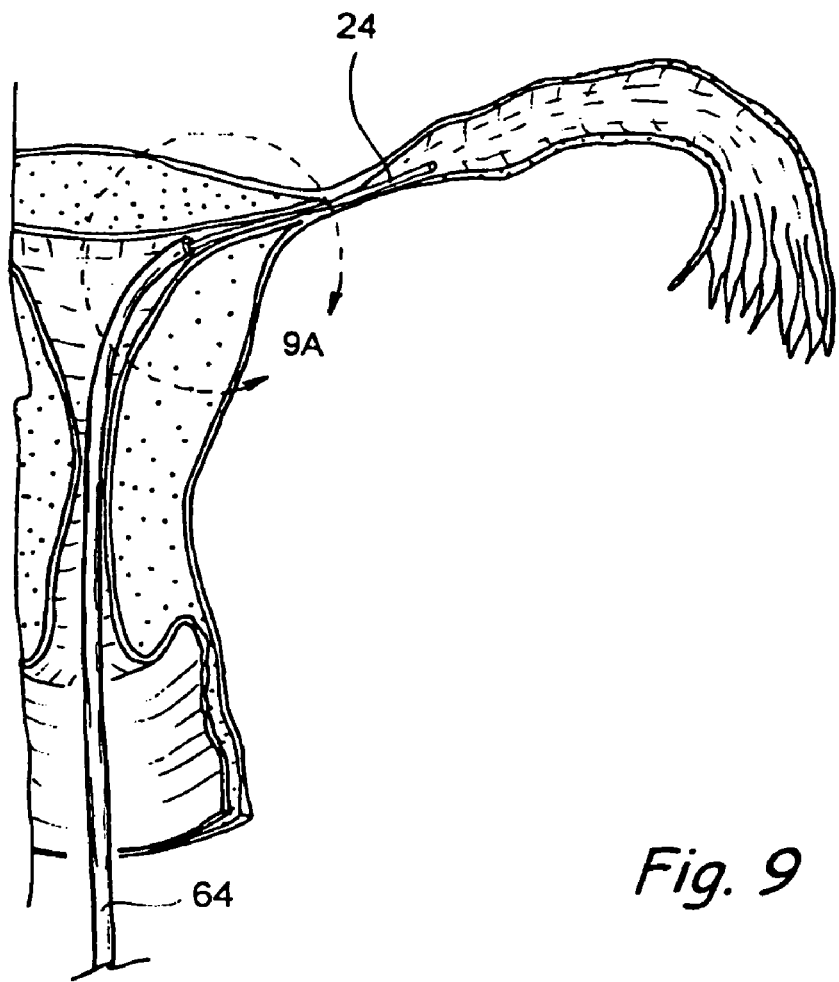
FIG. 9 is a sectional showing of the uterus and left fallopian tube of a human patient having a hysteroscope and a delivery system according to the present invention inserted into the left fallopian tube.
Figure 9A:
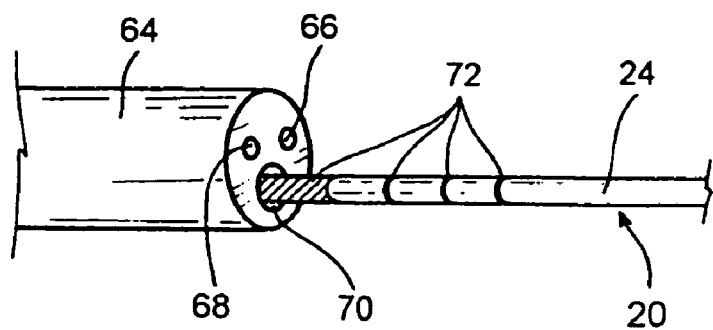
FIG. 9A is an enlarged view of the distal end of the hysteroscope and adjacent portion of segment 9A of FIG. 9, showing advancement of the delivery catheter out of a working channel of the hysteroscope.

FIGS. 9 and 9A show an example of a procedure wherein a hysteroscope 64 is used to view and/or facilitate implantation of a lumen occluding and/or substance delivery device 10. The hysteroscope 64 comprises an elongate, flexible device having a lumen or working channel 70, a light emission lens or port 68 and an image receiving lens or port 66. Initially, the hysteroscope 64 is advanced through the uterus UT and into the proximal fallopian tube FT, as shown. The delivery cannula 20 is then advanced through the working channel 70 of the hysteroscope 64. The physician may view, through the hysteroscope 64, the advancement of the delivery cannula 20 out of the distal end of the hysteroscope 64. Length indicating colored zone(s) and/or markings 72 may be provided at specific locations on the delivery cannula 20 to indicate to the length delivery cannula 20 that has been advanced from the distal end of the hysteroscope 64. Thus, the physician may advance the cannula 20 until he or she sees a specific colored zone or other length marking 72 which indicates that the cannula 20 has been advanced to the desired depth or location within the fallopian tube FT. length marking(s) 72 may be formed at locations on the delivery cannula 20 to indicate to the physician through the hysteroscope 64 that the distal end of the delivery cannula 20 has reached a desired implantation site distal to the fallopian tube ostium OS, typically within the intramural portion IMP of the fallopian tube FT or within the utero-tubal UTJ. In some cases the device 10 may be implanted elsewhere in the fallopian tube FT, such as in the isthmic region of the fallopian tube FT, distal to the isthmic region, or even in or near the ampulla region of the fallopian tube. In some embodiments, three separate markings 72 (e.g., 3 different colored zones or visible markings such as ruler type hash marks) the physician to selectively advance the delivery cannula 20 to one of several identified implantation sites (e.g., in the isthmus, between or spanning the transition between the isthmus and ampulla and in the ampulla. An alternative to visual means of determining the position or depth of insertion of the delivery cannula 20 is the use of ultrasound, electronic or image based guidance. In embodiments where ultrasound is used to determine the position of the delivery cannula 20, one or more echogenic marker(s) may be placed on the tip of or elsewhere on the delivery cannula 20 and/or on the implantable device 10 within the delivery cannula 20 to facilitate ultrasonic imaging and proper placement of the device 10 under ultrasonic guidance. Optionally, a physical barrier may be located on the delivery cannula 20 to prevent over-insertion.

Another means of placement for the device is under fluoroscopic guidance. In this case, one or more radiopaque marker(s) may be located on the tip of or elsewhere on the delivery cannula 20 and/or on the implantable device 10 within the delivery cannula 20 to facilitate positioning of the delivery cannula 20 and/or device 10 under fluoroscopy.

The lumen occluding and/or substance delivery device 10 may deliver (e.g., elute) substance(s) (e.g., drugs, therapeutic agents, biologics, proteins, spermicides, biological factors, cell preparations, friendly microbes, etc.) for some period of time following implantation into the body. In this regard, the device 10 may be of the configuration and structure shown in the figures and described hereabove, may be configured as a drug eluting substance such as fibers contained in a tubular structure, or may be of any other suitable configuration or structure. The rate and/or amount of substance delivered from the implanted device may be designed or controlled, in accordance with known drug delivery technology, to both control dosage (e.g. concentration in the uterus, fallopian tube, lung, tumor or other tissue, organ or anatomical structure), the location of delivery (e.g. systemic, local, topical, directed downstream in a feeding artery, etc.) and the time period over which the drug or other substance would be eluded or otherwise delivered by the implanted device. Also, in some aspects, the delivery of a substance from the device 10 may be responsive to a physical condition or presence/flow of a body fluid in the patient, such as a substance that is eluted by the device 10 and/or carried from the device 10 to another location as a result of the presence of certain conditions, such as different times in the menstrual cycle, or different blood chemistry conditions during the diurnal cycle, or different conditions as a result of physical or medical conditions such as the presence of certain biological factors, the blood pressure presented, the blood flow encountered, or the like.

The substance that is to be eluted or delivered from the implanted intraluminal device may be placed on or in the device 10 in various ways, examples of which are shown in FIGS. 5A-7B. For example, the device 10 or some portion thereof may be consist of or comprise a hollow member (e.g., a tube or hollow fiber) having a lumen or inner cavity wherein the substance is contained and the substance may then elute from that hollow member by diffusion through a wall or portion of the hollow member, by seepage or transport out of an aperture or opening formed in the hollow member, or by any other suitable means. FIG. 5 shows an example of the device 10 wherein a substance delivering matrix 18 is disposed on the device 10. This matrix 18 acts not only acts as a matrix (e.g., scaffold, form or support structure) for tissue ingrowth but also is coated with, impregnated with or contains a substance, such that the substance will elute from or otherwise be delivered from the matrix 18 following implantation of the device 10. FIG. 5A shows an example wherein the matrix 18 or a portion thereof is formed of a hollow member 18a (e.g., a hollow fiber) that has a lumen 38 wherein the substance is initially contained and a wall 36 through which the substance will diffuse or otherwise pass, thereby resulting in a release or elution of the substance from the hollow member 18a. FIG. 5B shows another example wherein the matrix 18 or a portion thereof is formed of a hollow member 18B that has a wall 40 and a lumen of inner cavity that opens through an opening 42 formed in one end or elsewhere in the wall 40 of the hollow member 18b such that substance contained in the lumen or inner cavity of the hollow member 18b will pass out of the opening 42, thereby resulting in a release or elution of the substance from the hollow member 18a. Each hollow member 18a, 18b may be extruded or otherwise formed such that its inner diameter, wall thickness and/or outlet opening size controls the rate at which the drug or other substance will be eluted from or delivered by the device 10. The amount of or depth to which the drug or other substance is loaded into each hollow member 18a, 18bcould control the dispersal of the drug over time (i.e. more drug in the hollow fiber will provide for a longer period of time over which the drug will be delivered). It will be appreciated that, additionally or alternatively, the hollow members 18a, 18b shown in FIGS. 5A and 5B could be used to form all or portions of the leg members 12 and/or 15 such that substance will elute from or be delivered by the leg members 12 and/or 15 in addition to or as an alternative to elution or delivery of substance from the matrix 18.

FIGS. 6-6C show other examples wherein all or portion(s) of the leg member(s) 12 and/or 15 are constructed to contain and deliver a drug or other substance. In some embodiments, all or portion(s) of the leg members 12 and/or 15 may be hollow, cellular, permeable or cavernous such that they may contain a drug or other substance (see FIGS. 6B and 6C) or one or more reservoir members may be attached to the device 10 to contain the drug or other substance (see FIG. 6A). The drug or other substance may then diffuse, leak, transport or otherwise pass out of the reservoir through semipermiable membrane(s) or openings.

For example, as shown in FIG. 6A, a semipermiable reservoir member 47 which contains the drug or other substance may be attached to the end of one or more leg(s) 12 such that the drug or substance will diffuse through the wall of the reservoir member 47 thereby delivering a therapeutically effective dose of the drug or substance to the subject over a desired period of time. The reservoir member 47 may or may not be removable from the implanted device 10 and, in some embodiments, the reservoir member 47 may be replaceable by another full reservoir member 47 in situ while the device 10 remains in place. For example, in applications where the device 10 is implanted within a fallopian tube FT for the purpose of contraception, the reservoir member 47 may be removed and/or replaced at a later date via a hysteroscope 64 and a suitable removal device such as a gripping device or forceps that may be passable through a working channel 70 of the scope 64. Alternatively, the reservoir member 47 may be refillable, for example by a syringe.

FIG. 6B shows an example wherein a portion 48 of a leg member 12 is hollow and contains the drug or substance and wherein a semipermiable window 50 is formed of material through which the drug or other substance will diffuse such that therapeutically effective dose of the drug or substance will be delivered to the subject over a desired period of time.

FIG. 6C shows an example wherein a portion 44 of a leg member 12 is hollow and contains the drug or substance and wherein a plurality of small holes 46 are formed in that portion of the leg 12 such that the drug or other substance will seep or otherwise flow out of the holes and a therapeutically effective dose of the drug or substance will be delivered to the subject over a desired period of time.

Additionally or alternatively, the substance may comprise or may be contained in particles (e.g., granules, beads, vesicles, blisters, bubbles, capsules, lyposomes, microcapsules, etc.) that are disposed on (e.g., adhered or affixed to) some portion of the device 10 such that the substance will be released is from the particles after the device 10 has been implanted.

Figure 7:
FIG. 7 is a side view of a lumen occluding/substance delivery device according to the present invention, disposed in a collapsed configuration and having a substance delivery reservoir thereon.
Figure 7A:
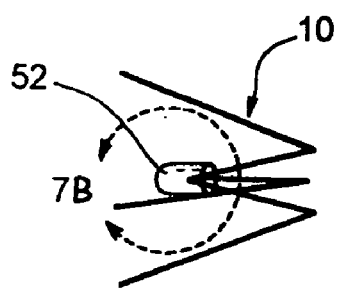
FIG. 7A is a side view of the device of FIG. 7 disposed in an expanded configuration.
Figure 7B:
FIG. 7B is an enlarged perspective view of the substance delivery reservoir of the device of FIGS. 7 and 7A.

FIGS. 7-7B show another example, wherein a substance delivering implant 52, such as a pellet or capsule, is separate from or may be attached to and/or associated with the lumen occluding and/or substance delivery device 10.

For example, in embodiments where the device 10 is implanted in a fallopian tube FT for contraceptive purposes, a contraceptive drug delivering implant 52 may be implanted proximally to, within, or distally to the device 10. The matrix of the pellet, in some embodiments, may be biodegradable (e.g., formed of polylactic acid, polyglycolic acid, etc.) such that after a desired or predetermined period of time, the pellet would dissolve and be gone. Methods for making substance delivering pellets or implants are previously known in the art including those described in U.S. Pat. Nos. 3,625,214; 3,991,750; 5,855,915 and 6,306,914, the entireties of which are expressly incorporated herein by reference.

It is to be appreciated that the drug or other substance may be incorporated into any portion or element of the device 10 in any suitable way. For example, the drug or substance may be mixed in to a material (e.g., a plastic) that flows, dissolves, melts, oozes or otherwise passes out of the device 10 following implantation. In such embodiments, the molecules of the drug or substance may be sized so as to migrate or pass between polymer chains of the plastic such that the drug or substance will leach or pass out of the plastic over a desired time period. In certain embodiments, the drug or substance may make up or be incorporated into a coating that is extruded or applied over all or a portion of the material located in or on the device, such that the drug or substance will elute or pass out of the coating at a desired rate or over a desired time period. In certain embodiments the drug or substance may make up or may be incorporated in a coating that is applied to all or a portion of the device 10 (e.g., the leg members 12 and/or 15 may be formed of a material such as self expanding nickel-titanium alloy or other metal and may be coated with a coating that consists of or contains the drug or substance) such that the drug or substance will elute or pass out of that coating at a desired rate or over a desired time period. In certain embodiments, one or more holes, indentations or other texture may be drilled or otherwise formed in the leg members 12 and/or 15 or the optional matrix 18 or other portion(s) of the device 10 and the desired drug or substance may be placed in the hole(s), indentation(s) or other texture such that the drug or substance will elute or pass out of the hole(s), indentation(s) or other texture over a desired time period. The diameter(s) and/or depth(s) of the hole(s), indentation(s) or other texture may be selected to control the rate and time over which the drug or substance will elute or otherwise pass from the device. In certain embodiments the substance may be responsive to the physiological conditions and thereby control the delivery of the substance in response to those conditions. For example, where the substance is released for contraceptive purposes within the fallopian tubes, the release of the substance may be controlled to some extent by the menstrual cycle of the patient. Certain well known biochemical conditions prevail within the uterus and fallopian tubes at the time and shortly after the release of the egg from the ovaries (referred to here as ovulation). A pellet of spermicidal substance or other similar contraceptive substance may be coated with a substance that is soluble in response to the biochemical conditions that prevail at the time of ovulation, but relatively insoluble in the biochemical conditions that prevail in the uterus and fallopian tubes at other times. This would result in the release of the substance primarily at the time of ovulation, and thus result in a long lasting contraceptive pellet that enhances contraception at precisely the time when it will be effective. Another example of the release of the substance in response to physiological conditions would be where a greater amount of substance is released in response to increased blood flow, as in a chemotherapeutic agent located in a feeding artery to a tumor. As the blood flow decreases, smaller amounts of the chemotherapeutic substance is released, resulting in decreased systemic effects as the blood flow to the tumor is cut off. Responses to blood pressure, diurnal cycles, and the like can also be engineered in accordance with this invention.

Figure 8:
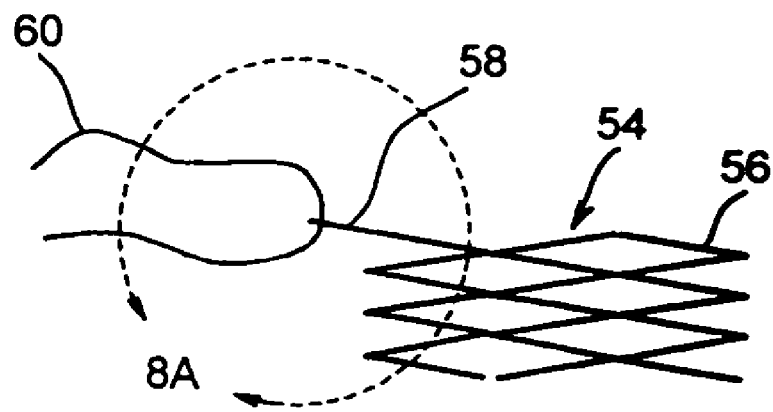
FIG. 8 is a perspective view of another embodiment of a lumen occluding/substance delivery device according to the present invention having an optional visualization member thereon.
Figure 8A:
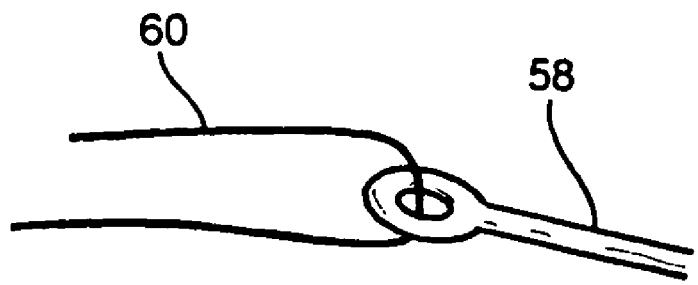
FIG. 8A is an enlarged view of a portion of the device of FIG. 8.

As shown in FIGS. 8 and 8A, the invention also provides an implantable lumen occluding and/or substance delivering device 54 that further comprises a flag or marker 60 that unravels or extends out of the fallopian tube and into the uterus for visual confirmation to indicate which fallopian tube has a device 54 in it. In this particular non-limiting example, the device 54 comprises a mesh body 56 that is designed to facilitate tissue ingrowth and occlude of a fallopian tube or other body lumen in which it is implanted. An arm 58 extends from the body 56 and the marker 60 is attached to the arm 58, as shown. Optionally, this flag or marker 60 and/or the body 56 of the device 54 can contain a substance (e.g., contraceptive drug, antifungal, antibiotic, agent for treatment of STD such as pelvic inflammatory disease, spermicidal agent, etc.) as described above. Also, optionally, this flag or marker 60 may be dissolvable or biodegradable and/or retrievable and removable at a later date, such through an endoscope or hysteroscope as described above. In embodiments, where the flag or marker 60 or any other component of the device is removable from the body, that component may contain substance(s), such as copper, that are desirable for only for short term implantation.

The substance eluting implantable devices 10, 54 of the present invention may be useable in various applications. For example, as described above, in applications where the device 10, 54 is implanted in a fallopian tube FT or elsewhere in the female genitourinary tract for the purpose of blocking egg migration or implantation, the device 10, 54 may additionally elute or deliver a female contraceptive agent or spermicidal agent to deter pregnancy, at least for some initial period of time following implantation of the intraluminal device. Any effective contraceptive or spermicidal agent may be used, in amounts that result in the desired therapeutic effect of avoiding pregnancy.

Specific examples of contraceptive agents that may be used include; the contraceptive hormone contained in the Norplant system (e.g., a synthetic progestin, namely, levonorgestrel having the molecular formula (d (−)-13-beta-ethyl-17-alpha-ethinyl-17-beta-hydroxygon-4-en-3-one) and a molecular weight of 312.45 and/or various other contraceptive hormone preparations including but not limited to medroxyprogesterone acetate, norethisterone enanthate, progestogen, levonorgestrel, levonorgestrel (as progestogen), ethinyl estradiol (as estrogen), norgestrel (as progestogen), levonorgestrel in combination with ethinyl estradiol, Norethisterone enanthate, norgestrel in combination with ethinyl estradiol, quinacrine, etc. Quinacrine is not a hormone. Rather, quinacrine is an agent which may be used to cause chemical, non-surgical female sterilization. When a quinacrine hydrocholoride pellet is inserted directly into the uterus, the guinacrine liquefies and flows into the fallopian tubes, causing permanent scarring. Although recorded failure rates and persistent side effects related to quinacrine sterilization have been low, controversy has developed around quinacrine's long-term safety, efficacy, and link to upper genital tract infections. However, direct placement of quinacrine into the fallopian tube in combination with or as part of a lumen blocking implantable device of this invention may permit the use or relatively low levels of quinacrine which would facilitate a local effect within the fallopian tube without untoward systemic toxicity.

In applications where the device 10 is implanted within a fallopian tube FT to cause contraception, the device 10 may deliver a contraceptive agent in an amount that a) causes an effect on the uterine tissue (e.g., endometrium) such that eggs will not become implanted within the uterus UT and/or b) causes cessation of ovulation. Typically, the dose of contraceptive substance delivered to cause cessation of ovulation is higher than the dose delivered to cause non-implantation of eggs in the endometrium. For example, the device 10 may deliver from about 10 micrograms to about 70 micrograms of levonorgestrel (d (−)-13-beta-ethyl-17-alpha-ethinyl-17-beta-hydroxygon-4-en-3-one). Dosages of levonorgestrel within the lower portion of this dosage range (e.g., from about 10 micrograms per day to about 30 micrograms per day) may be used to cause non-implantation of eggs in the endometrium while dosages within the higher portion of that dosage range (e.g., from about 30 micrograms per day to about 70 micrograms per day) may be used to cause cessation of ovulation. The dosages may vary however and this invention is not limited to any specific dosage or any specific agent. Indeed, the optimal dosage of a particular contraceptive agent to be delivered from the device 10 may depend on various factors, such as the age of the patient, the specific location at which the device 10 is implanted in the fallopian tube FT, whether devices 10 are implanted on only one or both fallopian tubes FT, etc.

Specific examples of specific spermicidal agents that may be used include but are not limited to nonoxynol-9, octoxynol-9, menfegol, benzalkonium chloride and N-docasanol.

Also, in any application where infection or microbial infestation is a concern, the device may elute or deliver antimicrobial agent(s) (e.g., microbicidal agents, antibiotics, antiviral agent(s), anti paracyte agent(s), etc.) Specific examples of antimicrobial agents that may be eluted or delivered from the implanted device include but are not limited to: Acyclovir; Amantadine; Aminoglycosides (e.g., Amikacin, Gentamicin and Tobramycin); Amoxicillin; Amoxicillin/Clavulanate; Amphotericin B; Ampicillin; Ampicillin/sulbactam; Atovaquone; Azithromycin; Cefazolin; Cefepime; Cefotaxime; Cefotetan; Cefpodoxime; Ceftazidime; Ceftizoxime; Ceftriaxone; Cefuroxime; Cephalexin; Chloramphenicol; Clotrimazole; Ciprofloxacin; Clarithromycin; Clindamycin; Dapsone; Dicloxacillin; Doxycycline; Erythromycin; Fluconazole; Foscarnet; Ganciclovir; Gatifloxacin; Imipenem/Cilastatin; Isoniazid, Itraconazole+(Sporanox®); Ketoconazole; Metronidazole; Nafcillin; Nafcillin; Nystatin; Penicillin; Penicillin G; Pentamidine; Piperacillin/Tazobactam; Rifampin; Quinupristin-Dalfopristin; Ticarcillin/clavulanate; Trimethoprim/Sulfamethoxazole; Valacyclovir; Vancomycin; Mafenide; Silver Sulfadiazine; Mupirocin; Nystatin; Triamcinolone/Nystatin; Clotrimazole/Betamethasone; Clotrimazole; Ketoconazole; Butoconazole; Miconazole; Tioconazole, detergent-like chemicals that disrupt or disable microbes (e.g., nonoxynol-9, octoxynol-9, benzalkonium chloride, menfegol, and N-docasanol); chemicals that block microbial attachment to target cells and/or inhibits entry of infectious pathogens (e.g., sulphated and sulponated polymers such as PC-515 (carrageenan), Pro-2000, and Dextrin 2 Sulphate); antiretroviral agents (e.g., PMPA gel) that prevent HIV or other retroviruses from replicating in the cells; genetically engineered or naturally occurring antibodies that combat pathogens such as anti-viral antibodies genetically engineered from plants known as "Plantibodies," agents which change the condition of the tissue to make it hostile to the pathogen (such as substances which alter vaginal pH (e.g., Buffer Gel and Acidform) or bacteria which cause the production of hydrogen peroxide within the vagina (e.g., *lactobacillus*).

Also, in some applications, a substance eluting implantable device may be placed in a body lumen (e.g., blood vessel, bronchus, hepatic duct, common bile duct, pancreatic duct, etc.) near a tumor and the device may deliver one or more anti-tumor agents to treat the tumor. Specific examples of anti-tumor agents that may be used in this invention include but are not limited to: alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU), Antitumor antibiotics and other compounds that act by binding or intercalating DNA and preventing RNA synthesis (e.g., doxorubicin, daunorubicin, epirubicin, idarubicin, mitomycin-C and bleomycin)Plant (vinca) alkaloids and other anti-tumor agents derived from plants (e.g., vincristine and vinblastine), Steroid hormones, hormone inhibitors, hormone receptor antagonists and other agents which affect the growth of hormone-responsive cancers (e.g., tamoxifen, herceptin, aromatase ingibitors such as aminoglutethamide and formestane, trriazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-1, meth-2, thalidomide (Thalomid), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, IMC-1C11, IM862, TNP-470, celecoxib (Celebrex), rofecoxib (Vioxx), interferon alpha, interleukin-12 (IL-12) or any of the compounds identified in *Science* Vol. 289, Pages 1197-1201 (Aug. 17, 2000)), biological response modifiers (e.g., interferon, bacillus calmette-guerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, flurouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol, taxotere, analogs/congeners and derivatives of such compounds as well as other antitumor agents not listed here.

Figure 10:
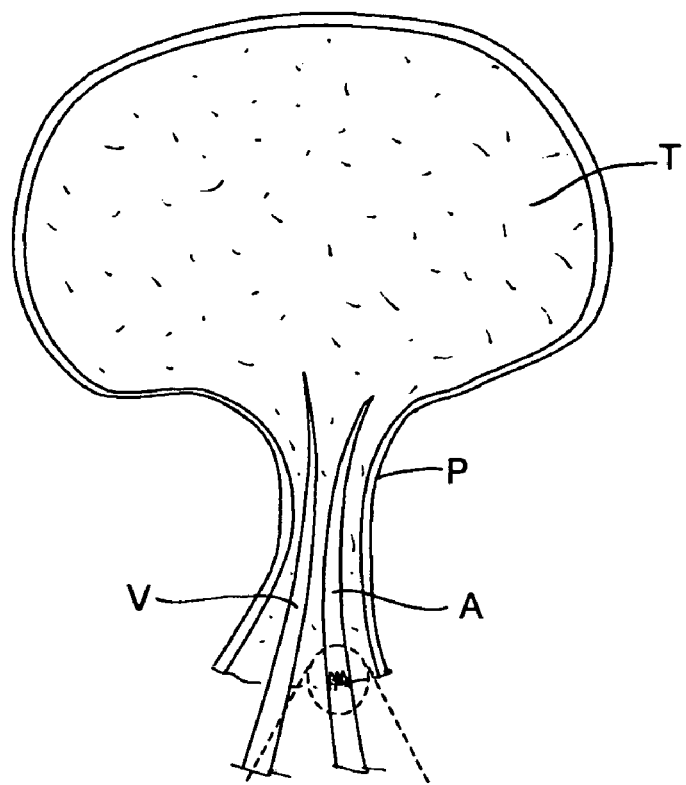
FIG. 10 is a schematic showing of the trachea and lungs of a human patient wherein a lumen occluding/substance delivery device of the present invention implanted in a bronchus of the patient's left lung.
Figure 10A:
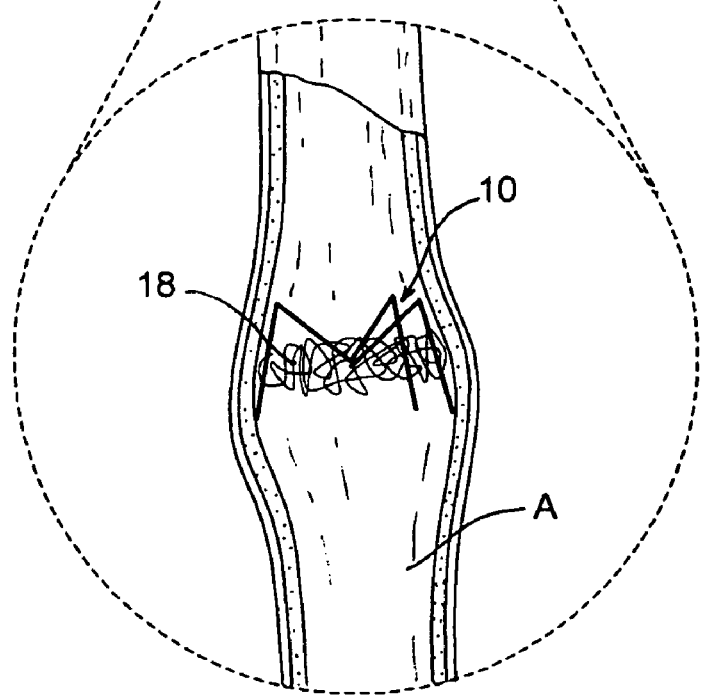
FIG. 10A is an enlarged sectional view of a bronchus of the left lung shown in FIG. 10 having a lumen occluding/substance delivery device of the present invention implanted therein.

In some embodiments the lumen occluding and/or substance delivering device 10, 54 may be used for antitumor applications. In the example shown in FIGS. 10 and 10A, a tumor T has a peduncle P through which and artery A and vein V run. A lumen occluding and/or substance delivering device 10 of the present invention is implanted in the artery A to occlude the artery A thereby cutting of blood flow to the tumor and/or to deliver an antineoplastic or antitumor substance to the tumor T. In some of these applications, the implanted device 10 may continue to allow some flow of blood or other body fluid through the body lumen in which it is positioned and into the tumor for at least an initial period of time following implantation of the device (e.g., until tissue ingrowth into the device 10 closes off the lumen of the blood vessel or other body lumen). In this way, the antitumor substance eluted or delivered by the device 10 will be carried into the tumor T for some desired period of time following implantation. Thereafter, cellular ingrowth into the device 10 causes a progressive and complete occlusion of the artery A after the desired dose of antitumor substance has been delivered to the tumor T. This blockage of blood flow to the tumor T may further serve to inhibit or kill some or all of any remaining tumor cells that have not been killed by the anti-tumor drug. The release of the drug may be controlled based on the rate of blood flow through the feeding vessel. As the artery A occludes over time, less total amount of the drug will be released into the bloodstream and thus there will be less systemic effects of the chemotherapeutic agent which will generally result in less dramatic side effects. On the other hand, the concentration of the antitumor substance will generally be slightly more concentrated in the blood based on the reduced flow, resulting in a more concentrated but more localized therapeutic effect on the tumor T.

Figure 11:
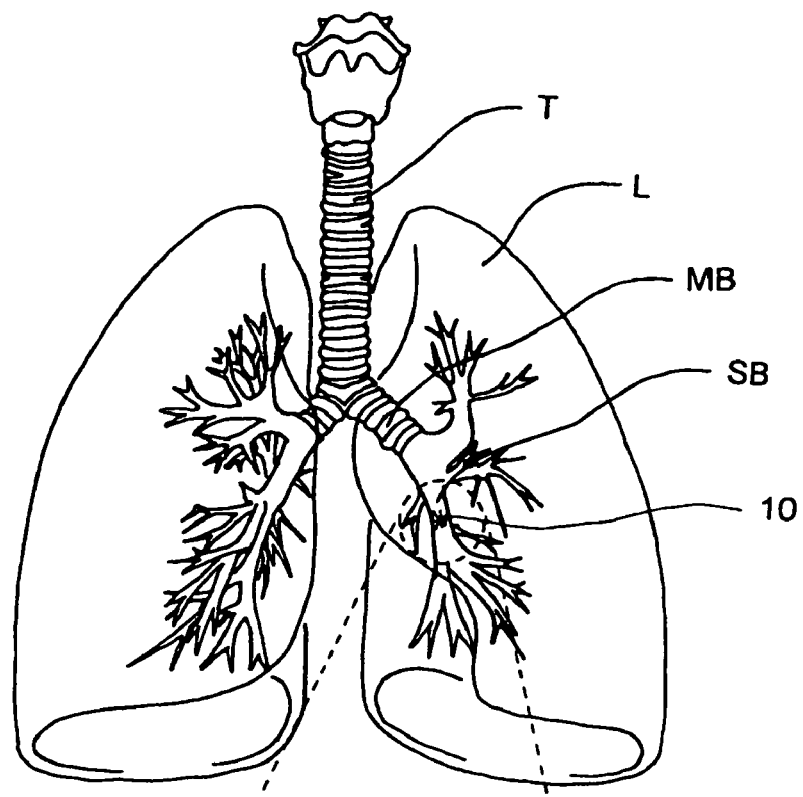
FIG. 11 is a view of the lungs of a patient into which an occlusive delivery device of the invention has been inserted.
Figure 11A:
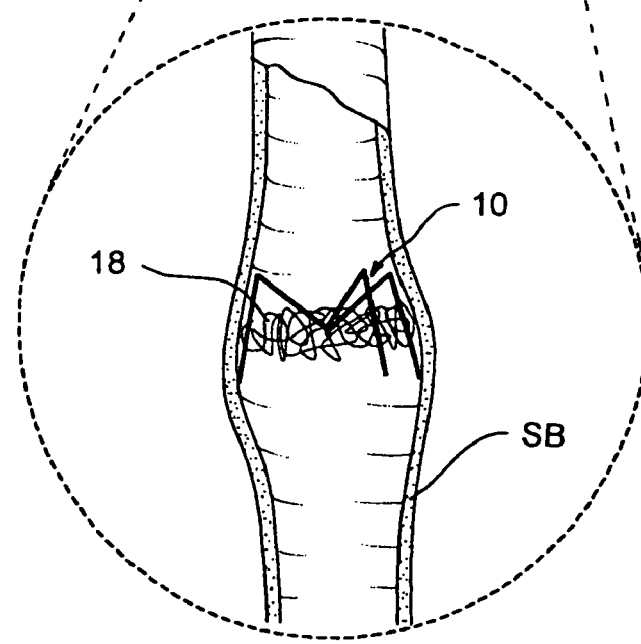
FIG. 11A is an expanded, partially cut-away view of the portion of FIG. 11 indicated by the dashed circle.
Figure 11B:
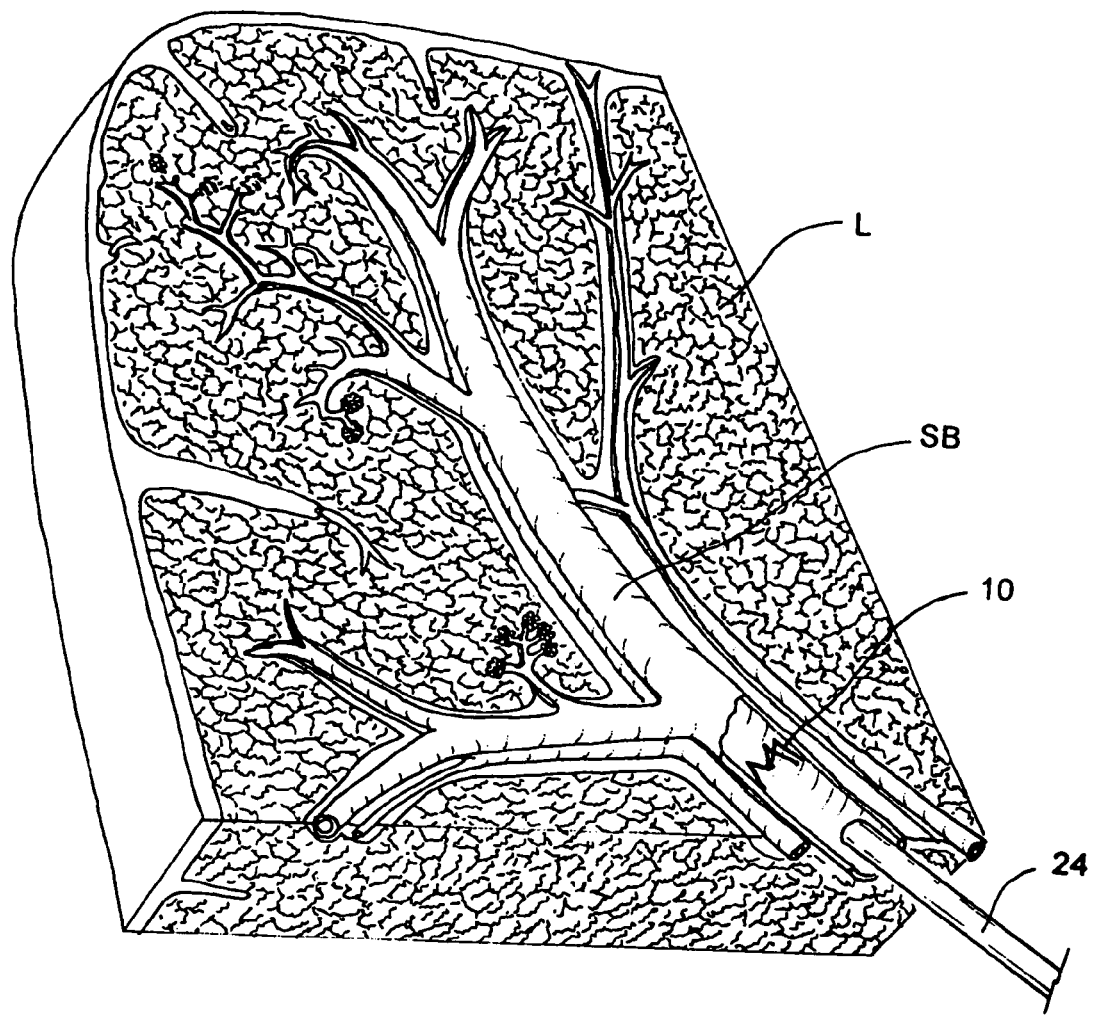
FIG. 11B is a cut-away view of a portion of a patient's lung showing the delivery catheter and the occlusive device in place.

In yet another example of an application of this invention shown in FIGS. 11-11B, the implantable intraluminal device 10 is implanted into a lung L to block air flow to a portion of the lung L. As seen in FIG. 11, the trachea T is bifurcated into right and left mainstem bronchi MB. Each mainstem bronchus MB then branches into a number of secondary bronchi SB. In the particular non-limiting example shown, the device 10 is implanted into a secondary bronchus SB that leads into the lower lobe of the left lung L. Following implantation, the device 10 may cause instant or progressive full occlusion of the secondary bronchus SB, so as to prevent air from entering the diseased lobe or region of lung parenchyma that receives air through that secondary bronchus SB. Such leakage or disease may result from, for example, a ruptured emphysematous bleb, traumatic lung puncture or iatrogenic lung rupture. In other cases the device 10 may be constructed so as not to substantially block airflow through the bronchus and possibly even to perform a scaffolding or stenting function which holds the lumen of the bronchus open. In either type of device, a drug or substance may be eluted or delivered by the device into the adjacent pulmonary tissue. For example, in cases where the device has been implanted to close off flow to a punctured area of the lung, the device may elute an antibiotic or other agent (e.g., a bronchodilator, mucolytic agent, expectorant, etc.) to locally deter or treat any infection or other condition present or developing in the lung tissue. In cases where the device 10 is implanted in a bronchus to treat emphysema or chronic obstructive pulmonary disease, the device may elute a therapeutic agent that is effective to treat that underlying condition or its symptoms.

Some examples of drugs that may be eluted from the device for the purpose of treating such lung diseases include but are not limited to: antimicrobial substances (examples of which are listed hereabove); corticosteroids such as beclomethasone (Vanceril, Beclovent), triamcinolone (Azmacort), flunisolide (Aerobid), fluticasone (Flovent), budesonide (Pulmicort), dexamethasone, prednisone, prednisolone, methylprednisolone (Medrol, SoluMedrol, DepoMedrol), methylprednisolone (Depo-Medrol), hydrocortisone (SoluCortef), methylprednisolone (SoluMedrol); Mediator-release inhibitors or cromones such as, cromolyn sodium (Intal), nedocromil sodium (Tilade); anti-leukotriene drugs such as leukotriene-receptor antagonists (e.g., zafirlukast (Accolate)), leukotriene-synthesis inhibitors (e.g., zileuton (Zyflo)) and other anti-leukotrienes (e.g., montelukast (Singulair)), mucolytic agents and expectorants (e.g., guifenisn); bronchodilator drugs such as beta-adrenergic agonists (e.g., epinephrine (Primatene), isoproterenol (Isuprel), isoetharine (Bronkosol), metaproterenol (Alupent, Metaprel), albuterol (Proventil, Ventolin), terbutaline (Bricanyl, Brethine), bitolterol (Tornalate), pirbuterol (Maxair), salmeterol (Serevent), Methyl xanthines (e.g., caffeine, theophylline, aminophylline and oxtriphylline (Choledyl)) and anticholinergics (e.g., atropine, ipratropium bromide (Atrovent).

It will be appreciated by those skilled in the art that various modifications, additions, deletions, combinations and changes may be made to the examples described hereabove and shown in the drawings, without departing from the intended spirit and scope of this invention. All such reasonable modifications, additions, deletions, combinations and changes are included in this disclosure.

What is claimed is:

1. A device for implantation within a body lumen of a human or veterinary subject, said device comprising:
    an intraluminal member having at least three radially-expandable legs, each of said legs including first and second segments joined at an apex, said second segment being in a radially-expandable, spaced-apart relationship from said first segment such that an acute angle is formed between said first and second joined segments in the expanded configuration, at least one of said legs including a lumen therewithin in the expanded configuration and openings on the surface of said legs, said openings comprising semi-permeable membranes, said intraluminal member including a fibrous matrix disposed within the confines of the radially expandable legs, the intraluminal member being implantable in a body lumen having a wall, the fibrous matrix structured to promote tissue or cellular ingrowth from the lumen wall into the fibrous matrix disposed in the intraluminal member, said tissue or cellular ingrowth causing occlusion of the body lumen; and
    a quantity of therapeutic substance contained within said at least one leg lumen such that the therapeutic substance will be delivered from the lumen of said leg through the semi-permeable membrane to a target tissue for a period of time following implantation of the intraluminal member within the body lumen.

2. A device for implantation within a body lumen of a human or veterinary subject, said device comprising:
    an intraluminal member having at least three radially expandable legs, each of said legs including first and second segments joined at an apex, said second segment being in a radially-expandable, spaced-apart relationship from said first segment such that an acute angle is formed between said first and second joined segments in the expanded configuration, at least one of said legs including a cavity therewithin in the expanded configuration and a plurality of openings comprising semi-permeable membranes on the surface of said at least one leg, the intraluminal member structured to be implantable in a body lumen having a wall and configured to facilitate tissue or cellular ingrowth from the lumen wall into the intraluminal member to cause occlusion of the body lumen; and
    a quantity of therapeutic substance initially contained within the cavity of the at least one leg such that the therapeutic substance will be delivered from said cavity through the semi-permeable membranes of the at least one leg to a target tissue for at least some period of time following implantation of the intraluminal member within the body lumen.

3. A device for implantation within a body lumen of a human or veterinary subject, said device comprising:
    an intraluminal member comprising at least three radially expandable legs, each of said legs including first and second segments joined at an apex, said second segment being in a radially-expandable, spaced-apart relationship from said first segment such that an acute angle is formed between said first and second joined segments in the expanded configuration; at least one leg comprising semi-permeable membranes disposed within openings of said at least one leg, said at least one leg having a lumen containing a quantity of therapeutic substance therewithin, the intraluminal member being implantable in a body lumen having a wall and configured to facilitate tissue or cellular ingrowth from said body lumen wall onto the intraluminal member to cause occlusion of the body lumen,
    wherein said quantity of therapeutic substance diffuses through said semi-permeable membranes to a target tissue for a period of time following implantation of the intraluminal member within the body lumen.

4. A device according to claim 1, 2 or 3 wherein the device is implantable in a body lumen comprising a fallopian tube or other lumen of the female reproductive tract and is effective to occlude that lumen following implantation.

5. A device according to claim 4 wherein the therapeutic substance delivered by the device comprises a contraceptive.

6. A device according to claim 5 wherein the contraceptive device substance is selected from the group consisting of:
    synthetic progestins, levonorgestrel, medroxyprogesterone acetate, norethisterone enanthate, progestogen, levonorgestrel, levonorgestrel (as progestogen), ethinyl estradiol (as estrogen), norgestrel (as progestogen), levonorgestrel in combination with ethinyl estradiol, norethisterone enanthate, norgestrel in combination with ethinyl estradiol and quinacrine.

7. A device according to claim 4 wherein the therapeutic substance delivered by the device comprises a spermicidal agent.

8. A device according to claim 7 wherein the spermicidal agent is selected from the group consisting of: nonoxynol-9, octoxynol-9, menfegol, benzalkonium chloride and N-docasanol.

9. A device according to claim 4 wherein the therapeutic substance delivered by the device comprises an antimicrobial agent.

10. A device according to claim 9 wherein the antimicrobial agent is selected form the group consisting of: acyclovir, an aminoglycoside, gentamicin, tobramycin, amoxicillin, amoxicillin+clavulanate, amphotericin B, ampicillin, ampicillin/sulbactam, atovaquone, azithromycin, cefazolin, cefepime, cefotaxime, cefotetan, cefpodoxime, cefiazidime, ceflizoxime, ceftriaxone, ceftiroxime, cephalexin, chloramphenicol, clotrimazole, ciprofloxacin, clarithromycin, clindamycin, dapsone, dicloxacillin, doxycycline, erythromycin, fluconazole, foscarnet, ganciclovir, gatifloxacin, imipenem, cilastatin, imipenem+cilastatin, isoniazid, itraconazole, ketoconazole, metronidazole, nafcillin, nafcillin, nystatin, penicillin, penicillin G, pentamidine, piperacillin, tazobactam, piperacillin+tazobactam; rifampin, quinupristin, dalfopristin, quinupristin+dalfopristin, ticarcillin, clavulanate, ticarcillin+clavulanate, trimethoprim, sulfamethoxazole, trimethoprim+sulfamethoxazole, valacyclovir, vancomycin, mafenide, silver sulfadiazine, mupirocin, nystatin, triamcinolone, nystatin, triamcinolone+nystatin, clotrimazole+betamethasone, butoconazole, miconazole, tioconazole, a detergent-like substances that disrupt or disable microbes, nonoxynol-9, octoxynol-9, benzalkonium chloride, menfegol, N-docasanol, a chemical that blocks microbial attachment to target cells and/or inhibits entry of infectious pathogens into cells, sulphated and sulponated polymers, carrageenan, Pro-2000, dextrin 2 sulphate, antiretroviral agents, PMPA gel, genetically engineered or naturally occurring antibodies that combat pathogens, agents which change the condition of the tissue to make it hostile to the pathogen, substances which alter vaginal pH, buffer gel, acidform, microbes that cause the production of hydrogen peroxide within the vagina, and lactobacillus.

11. A device according to claims 1, 2 or 3, wherein the device is implanted in a lumen of the vas deferens or other lumen of the male reproductive tract and is effective to occlude that lumen following implantation.

12. A device according to claim 11 wherein the therapeutic substance delivered by the device comprises a spermicidal agent.

13. A device according to claim 12 wherein the spermicidal agent is selected from the group consisting of: nonoxynol-9, octoxynol-9, menfegol, benzalkonium chloride and N-docasanol.

14. A system for causing contraception in a human or animal subject, said system comprising:

an expandable occluding member implantable in a reproductive passageway of the subject, the reproductive passageway having a wall, the expandable occluding member configured to facilitate tissue or cellular ingrowth from the wall of the passageway into the expandable occluding member, said occluding member being a) disposable in a first configuration wherein it is sufficiently compact to allow the occluding member to be advanced into the reproductive passageway and b) subsequently expandable to a second configuration wherein the occluding member engages the wall of the reproductive passageway, said occluding member having at least three radially-expandable legs, each of said legs including first and second segments joined at an apex, said second segment being in a radially-expandable, spaced-apart relationship from said first segment, wherein an acute angle is formed between said first and second joined segments in the expanded second configuration;

each of said legs including a lumen therewithin and comprising at least one semi-permeable membrane on a surface thereof; and a quantity of contraceptive substance which diffuses from the lumen of said hollow fiber membranes in sufficient amount to cause a pharmacologic contraceptive effect in the patient for a period of time following implantation of the occluding member within the reproductive passageway to enhance contraception.

15. A system according to claim 14 wherein the occluding member further comprises means for securing the occluding member to the wall of the reproductive passageway.

16. A system according to claim 15 wherein the means for securing the occluding member to the wall of the reproductive passageway comprises a mechanical securing apparatus.

17. A system for causing contraception in a human or animal subject, said system comprising:

an expandable occluding member implantable in a reproductive passageway of the subject, the reproductive passageway having a wall, the expandable occluding member configured to facilitate tissue or cellular ingrowth from said passageway wall into the expandable occluding member said occluding member being a) disposable in a first configuration wherein it is sufficiently compact to allow the occluding member to be advanced into the reproductive passageway and b) subsequently expandable to a second configuration wherein the occluding member engages the wall of the reproductive passageway, said expandable occluding member including at least three radially expandable plurality of legs, each of said legs including first and second segments joined at an apex, said second segment being in a radially-expandable, spaced-apart relationship from said first segment such that an acute angle is formed between said first and second joined segments in the expanded second configuration, at least one of said legs including a cavity therewithin in the expanded second configuration and a plurality of semi-permeable windows on a surface thereof; and a quantity of contraceptive substance which is delivered from said cavity through said semi-permeable windows in sufficient amount to cause a pharmacologic contraceptive effect in the patient for a period of time following implantation of the occluding member within the reproductive passageway, wherein the occluding member further comprises means for securing the occluding member to the wall of the reproductive passageway and wherein the means for securing the occluding member to the wall of a reproductive passageway comprises an adhesive.

18. A system according to claim 14 or 17 wherein the substance comprises a hormone.

19. A system according to claim 18 wherein the substance comprises a progestin.

20. A system according to claim 18 wherein the substance comprises a synthetic progestin.

21. A system according to claim 14 or 17 wherein the substance comprises levonorgestrel.

22. A system according to claim 14 or 17 wherein the substance comprises (d(-)-13-beta-ethyl-17-alpha-ethinyl-17-beta-hydroxygon-4-en-3-one).

23. A system according to claim 14 or 17 wherein the substance comprises (d(-)-13-beta-ethyl-17-alpha-ethinyl-17-beta-hydroxygon-4-en-3-one) having a molecular weight of 312.45.

24. A system according to claim 14 or 17 wherein the occluding member is sized and configured to be implanted within the lumen of a fallopian tube.

25. A system according to claim 14 or 17 wherein the occluding member causes a reversible occlusion of the reproductive passageway.

26. A system according to claim 25 wherein the occlusion of the reproductive passageway is reversible by removing at least a portion of the occluding member and any tissue that has grown into the occluding member or that portion of the occluding member.

* * * * *